United States Patent
Bromidge

(10) Patent No.: US 6,313,145 B1
(45) Date of Patent: *Nov. 6, 2001

(54) INDOLINE DERIVATIVES USEFUL AS 5-HT-2C RECEPTOR ANTAGONISTS

(75) Inventor: Steven Mark Bromidge, Harlow (GB)

(73) Assignee: SmithKline Beecham p.l.c., Brentford (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/202,772

(22) PCT Filed: Jun. 16, 1997

(86) PCT No.: PCT/EP97/03157

§ 371 Date: Dec. 21, 1998

§ 102(e) Date: Dec. 21, 1998

(87) PCT Pub. No.: WO97/48700

PCT Pub. Date: Dec. 24, 1997

(30) Foreign Application Priority Data

Jun. 20, 1996 (GB) .................................................. 9612885

(51) Int. Cl.$^7$ ...................... A61K 31/4439; A61F 25/24; C07D 401/14

(52) U.S. Cl. ............................................. 514/333; 546/256
(58) Field of Search ............................... 514/333; 546/256

(56) References Cited

U.S. PATENT DOCUMENTS 6,028,055    2/2000   Lowe et al. .

FOREIGN PATENT DOCUMENTS

| WO 94/04533 | 3/1994 | (WO) . |
| WO 95/01976 | 1/1995 | (WO) . |
| WO 96/23783 | 8/1996 | (WO) . |
| WO 97/37989 | 8/1996 | (WO) . |
| WO 96/23769 | 10/1997 | (WO) . |

OTHER PUBLICATIONS

Cram and Hammond, "Organic Chemistry", McGraw Hill Book Co., NY (1964) 2nd ed., pp 565–67.*

* cited by examiner

*Primary Examiner*—Patricia L. Morris
(74) *Attorney, Agent, or Firm*—Soma G. Simon; William T. King; Charles M. Kinzig

(57) ABSTRACT

Indoline derivatives useful as $5HT_{2C}$ receptor antagonists and methods of using them to treat various CNS disorders are provided.

10 Claims, No Drawings

INDOLINE DERIVATIVES USEFUL AS 5-HT-2C RECEPTOR ANTAGONISTS

This invention relates to compounds having pharmacological activity, processes for their preparation, to compositions containing them and to their use in the treatment of CNS disorders.

PCT/EP96/00368 (SmithKline Beecham plc) describes indole and indoline derivatives which are described as possessing $5HT_{2C/2B}$ receptor antagonist activity. A novel class of compounds has now been discovered which fall within the generic scope of PCT/EP96/00368, but are not specifically disclosed therein, and have been found to exhibit a surprisingly enhanced $5HT_{2C}$ receptor antagonist activity profile (enhanced activity and duration of action after oral dosing). $5HT_2C$ receptor antagonists are believed to be of potential use in the treatment of CNS disorders such as anxiety, depression, epilepsy, obsessive compulsive disorders, migraine, Alzheimers disease, sleep disorders, feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Compounds of the invention are also expected to be of use in the treatment of certain GI (gastrointestinal) disorders such as IBS (Irritable Bowel Syndrome) as well as microvascular diseases such as macular oedema and retinopathy.

The present invention therefore provides, in a first aspect, a compound of formula (I) or a salt thereof:

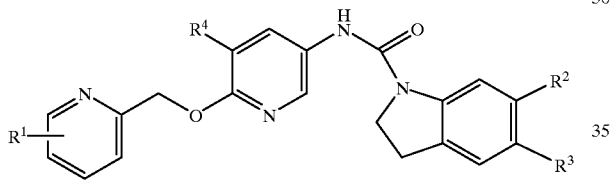

wherein:
$R^1$ is hydrogen or $C_{1-6}$ alkyl;
$R^2$, $R^3$ and $R^4$ groups are independently hydrogen, halogen or $C_{1-6}$ alkyl optionally substituted by one or more fluorine atoms.

$C_{1-6}$ Alkyl groups, whether alone or as part of another group, may be straight chain or branched.

Suitably $R^1$ is hydrogen or $C_{1-6}$ alkyl, preferably $R^1$ is hydrogen.

Suitably $R^2$, $R^3$ and $R^4$ groups are independently hydrogen, halogen or $C_{1-6}$ alkyl optionally substituted by one or more fluorine atoms. Preferably $R^2$ is $C_{1-6}$ alkyl substituted by one or more fluorine atoms, particularly $CF_3$ and $R^3$ is $C_{1-6}$ alkyl, particularly methyl or $R^2$ is hydrogen and $R^3$ is halogen, particularly bromine or $C_{1-6}$ alkyl substituted by one or more fluorine atoms, particularly $CF_3$. Preferably $R^4$ is hydrogen or $C_{1-6}$ alkyl, in particular methyl.

Particular compounds of the invention include:
5-Methyl-1-[2-(pyridin-2-ylmethyloxy)pyridin-5-ylcarbamoyl]-6-trifluoromethylindoline,
1-[2-(pyridin-2-ylmethyloxy)pyridin-5-ylcarbamoyl]-5-trifluoromethylindoline, 5-Methyl-1-[2-(pyridin-2-ylmethyloxy)-3-methylpyridin-5-ylcarbamoyl]-6-trifluoromethylindoline,
5-Bromo-1-[2-(pyridin-2-ylmethyloxy)pyridin-5-ylcarbamoyl]-indoline,
1-[2-(Pyridin-2-ylmethyloxy)pyridin-5-ylcarbamoyl]-6-trifluoromethyl-indoline, and pharmaceutically acceptable salts thereof.

The compounds of the formula (I) can form acid addition salts with acids, such as conventional pharmaceutically acceptable acids, for example maleic, hydrochloric, hydrobromic, phosphoric, acetic, fumaric, salicylic, citric, lactic, mandelic, tartaric and methanesulphonic.

Compounds of formula (I) may also form N-oxides or solvates such as hydrates, and the invention also extends to these forms. When referred to herein, it is understood that the term 'compound of formula (I)' also includes these forms.

Certain compounds of formula (I) are capable of existing in stereoisomeric forms including enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The compounds of the invention can be prepared using standard procedures such as those of PCT/EP96100368. for example by the coupling of a compound of formula (II);

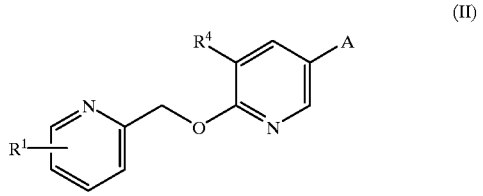

with a compound of formula (III);

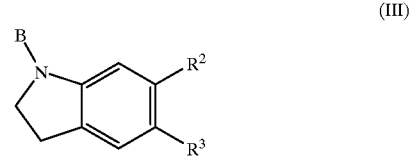

in which $R^1$, $R^2$, $R^3$ and $R^4$ are as defined in formula (I) and A and B contain the appropriate functional group(s) necessary to form the moiety —NHCO— when coupled and thereafter optionally forming a pharmaceutically acceptable salt thereof Suitable examples of groups A and B include:
 (i) A is —N═C═O and B is hydrogen,
 (ii) A is —NHCOL and B is hydrogen,
 (iii) A is —NH₂ and B is COL, or
 (iv) A is halogen and B is —CONH₂
wherein L is a leaving group. Examples of suitable leaving groups L include halogen such as chloro, bromo, imidazole, or phenoxy or phenylthio optionally substituted, for example, with one or more halogens.

Compounds of formula (II) and (III) may be prepared according to known methods or analogous to known methods, for example using the procedures described in WO 95/01976 and PCT/EP96/00368.

Novel intermediates of formula (II) and (III) also form part of the invention.

Pharmaceutically acceptable salts may be prepared conventionally by reaction with the appropriate acid or acid derivative. N-oxides may be formed conventionally by reaction with hydrogen peroxide or percarboxylic acids.

Compounds of formula (I) and their pharmaceutically acceptable salts have $5HT_{2C}$ receptor antagonist activity and are believed to be of potential use for the treatment or prophylaxsis of CNS disorders such as anxiety, depression, epilepsy, obsessive compulsive disorders, migraine, Alzheimers disease, sleep disorders (including disturbances of Circadian rhythym), feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Compounds of the invention are also expected to be of use in the treatment of certain GI disorders such as IBS as well as microvascular diseases such as macular oedema and retinopathy.

Thus the invention also provides a compound of formula (I) or a pharmaceutically acceptable salt thereof, for use as a therapeutic substance, in particular in the treatment or prophylaxis of the above disorders.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for the treatment or prophylaxis of the above disorders.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 20.0 mg, for example 0.2 to 5 mg; and such unit doses may be administered more than once a day, for example two or three a day, so that the total daily dosage is in the range of about 0.5 to 100 mg; and such therapy may extend for a number of weeks or months.

When administered in accordance with the invention, no unacceptable toxicological effects are expected with the compounds of the invention.

The following Descriptions and Examples illustrate the preparation of compounds of the invention.

DESCRIPTION 1

5-Nitro-2-(pyridin-2-ylmethyloxy)pyridine (D1)

2-Pyridylcarbinol (7.5 g, 0.069 mole) in dry dimethylformamide (190 ml) was cooled to −20° C. and treated with an 80% dispersion of sodium hydride in mineral oil (2.07 g, 0.069 mole) under argon. The mixture was stirred at −20° C. for two hours. 2-Chloro-5-nitropyridine (8.83 g, 0.058 mole) was added and the mixture was stirred at −20° C. for 0.5 hour then warmed to room temperature and stirred for 18 hours. Water was added dropwise and the solvent removed in vacuo. The residue was dissolved in dichloromethane, washed with 10% aqueous sodium hydroxide solution followed by water, dried ($Na_2SO_4$) and evaporated in vacuo to afford the title compound (12.2 g, 91%) as an orange solid.

$^1$H NMR (250 MHz; $CDCl_3$) (ppm): 5.61 (2H, s), 6.98 (1H, d, J=8), 7.21–7.31 (1H,m), 7.45 (1H, d, J=8), 7.73 (1H, dt, J=2,7), 8.40 (1H, dd, J=3,8), 8.65 (1H, d, J=3), 9.10 (1H, d, J=2).

DESCRIPTION 2

5-Amino-2-(pyridin-2-ylmethyloxy)pyridine (12)

5-Nitro-2-(pyridin-2-ylmethyloxy)pyridine (D1, 2.0 g, 0.0087 mole) in ethanol (70 ml) was treated with tin (II) chloride (8.3 g, 0.044 mole) in conc. HCl (15 ml). The mixture was heated to 50° C. for 0.5 hour. After cooling to room temperature, the mixture was diluted with water, basified with 10% aqueous sodium hydroxide solution, extracted into ethyl acetate, dried ($Na_2SO_4$) and evaporated in vacuo to afford the title compound (1.36 g, 78%) as a brown oil.

$^1$H NMR (200 MHz; $CDCl_3$) (ppm): 3.38 (2H, br s), 5.43 (2H, s), 6.73 (1H, d, J=8), 7.06 (1H, dd, J=3,9), 7.13–7.26 (1H, m), 7.45 (1H, d, J=8), 7.58–7.77 (2H, m), 8.60 (1H, d, J=5).

DESCRIPTION 3

Phenyl N-[2-(pyridin-2-ylmethyloxy)pyridin-5-yl] carbamate (D3)

5-Amino-2-(pyridin-2-ylmethyloxy)pyridine (D2, 1.36 g, 0.0068 mole) in dichloromethane (50 ml) was cooled to 0°

C. under argon. Triethylamine (1.04 ml, 0.0075 mole) was added, followed dropwise by phenyl chloroformate (0.94 ml, 0.0075 mole) and the mixture was stirred at room temperature for 4 hours, washed with water, dried ($Na_2SO_4$) and evaporated in vacuo. The residue was chromatographed on silica gel, eluting with ethyl acetate to leave the title compound (1.9 g, 87%) as a solid.

$^1$H NMR (250 MHz; $CDCl_3$) δ (ppm): 5.49 (2H, s), 6.85 (1H, d, J=7), 7.08–7.50 (8H, m), 7.70 (1H, dt, J=2,8),7.91 (1H, d, J=7),8.14 (1H, d, J=3),8.62 (1H, d, J=3).

DESCRIPTION 4

(2-Nitro-5trifluoromethylphenyl)acetonitrile (D4)

4-Nitrobenzotrifluoride (5 g, 0.026 mole) and 4-chlorophenoxyacetonitrile (4.86 g, 0.029 mole) in dry DMF (50 ml) were added dropwise to a solution of potassium-t-butoxide (6.4 g, 0.057 mole) in dry DMF (30 ml) under argon at −10° C. over 1 hour. The mixture was stirred at −10° C. for a further 3 hours, after which it was poured into 5N HCl/ice water (1:1) (300 ml) and extracted into DCM (3×200 ml). The DCM extract was washed with 10% aqueous sodium hydroxide solution, 5N hydrochloric acid and brine, dried ($Na_2SO_4$) and evaporated in vacuo. The resulting oil was chromatographed on silica gel eluting with 20% ethyl acetate/60–80° petroleum ether to afford the title compound (1.9 g, 32%) as an orange oil.

$^1$H NMR (200 MHz; $CDCl_3$) δ (ppm): 4.26 (2H, s), 7.87 (1H, d, J=8), 8.02 (1H, s), 8.31 (1H, d, J=8).

DESCRIPTION 5

5-Trifluoromethylindole (D5)

(2-Nitro-5-trifluoromethylphenyl)acetonitrile (D4, 1.9 g, 0.0088 mole) in 90% $EtOH/H_2O$ (25 ml) and glacial acetic acid (0.25 ml) was hydrogenated at 50 psi in the presence of 10% Pd/C (1 g) at room temperature for 2 hours. After filtration of the catalyst through kieselguhr, the solvent was removed in vacuo. The residue was basified with saturated aqueous potassium carbonate solution, extracted into DCM, dried ($Na_2SO_4$) and evaporated in vacuo. The residue was chromatographed on silica gel eluting with 30% ethyl acetate/60–80° petroleum ether to afford the title compound (1.0 g, 65%) as an off white solid.

$^1$H NMR (200 MHz; $CDCl_3$) δ (ppm): 6.65 (1H, t, J=1), 7.30 (1H, t, J=1), 7.36–7.58 (2H, m), 7.94 (1H, s), 8.34 (1H, br s)

DESCRIPTION 6

5-Trifluoromethylindoline (D6)

5-Trifluoromethylindole (D5, 1.0 g, 0.0057 mole) in glacial acetic acid (25 ml) was treated with sodium cyanoborohydride (1.7 g, 0.027 mole) under argon and stirred at room temperature for 2 hours. The mixture was poured into water (200 ml), basified with 40% aqueous sodium hydroxide solution, extracted into DCM, dried ($Na_2SO_4$) and evaporated in vacuo. The residue was chromatographed on silica gel eluting with 20% ethyl acetate/60–80° petroleum ether to afford the title compound (0.45 g, 45%) as a pale yellow oil.

$^1$H NMR (250 MHz; $CDCl_3$) δ (ppm): 3.07 (2H, t, J=8), 3.65 (2H, t, J=8), 4.02 (1H, br s), 6.60 (1H, d, J=7), 7.28 (1H, t, J=2), 7.30 (1H, s).

DESCRIPTION 7

(5-Methoxy-2-nitro4-trifluoromethylphenyl)acetonitrile (D7)

A mixture of 1-Methoxy4-nitro-2-trifluoromethylbenzene (93 g, 0.421 mol) and 4 chlorophenoxyacetonitrile (77.55 g, 0.463 mol) in dry DMF (500 ml) was added dropwise over 0.75 h to a stirred solution of KO$^t$Bu (103.85 g, 0.927 mol) in dry DMF (400 ml) at −10° C. After complete addition the resulting purple solution was maintained at −10° C. for 1 h then poured into a mixture of ice/water (1.5 l) and 5 M aqueous HCl (1.5 l). The resulting mixture was extracted with dichloromethane (3×1 l). The combined extracts were washed with water (3 l), dried ($Na_2SO_4$) and evaporated under reduced pressure. The residue was chromatographed on silica using 10–40% ethyl acetate/petroleum ether as eluant to give the crude product which was recrystallised from ethyl acetate/petroleum ether to afford the title compound (85.13 g, 78%) as a white solid. Mp 103–104° C.

$^1$H NMR ($CDCl_3$) δ: 4.10 (3H, s), 4.37 (2H, s), 7.34 (1H, s), 8.53 (1H, s).

DESCRIPTION 8

5-Methoxy-6-trifluoromethylindole (D8)

(5-Methoxy-2-nitro4-trifluoromethylphenyl)acetonitrile (D7) (85 g, 0.327 mol) in ethanol/water (9:1, 1.6 l) and glacial acetic acid (16 ml) was hydrogenated over 10% palladium on carbon (50 g) at 50 psi for 0.5 h at room temperature. The reaction mixture was filtered and evaporated in vacuo. The residue was partitioned between aqueous $K_2CO_3$ (1 l) and dichloromethane (2×1 l) and the combined organic extract was dried ($Na_2SO_4$) and evaporated to afford the title indole (67.63 g, 96%) as a grey solid.

$^1$H NMR ($CDCl_3$) δ: 3.94 (3H, s), 6.53 (1H, m), 7.21 (1H, s), 7.32 (1H, m), 7.64 (1H, s), 8.25 (1H, br s).

DESCRIPTION 9

5-Methoxy-6trifluoromethylindoline (D9)

The indole (D8) (67.63 g, 0.315 mol) in glacial acetic acid (500 ml) was treated with sodium cyanoborohydride (40 g, 0.637 mol) at room temperature with stirring. After 3 h at room temperature the reaction mixture was diluted with water (500 ml) and basified with 40% aqueous NaOH with cooling. The mixture was then extracted with dichloromethane (3×500 ml) and the combined extracts were dried ($Na_2SO_4$) and evaporated to give the title compound (67.73 g, 99%) as an off-white solid.

$^1$H NMR ($CDCl_3$) δ: 3.07 (2H, t), 3.58 (2H, t), 3.67 (1H, br s), 3.83 (3H, s), 6.83 (1H, s), 6.88 (1H, s).

DESCRIPTION 10

5-Hydroxy-6-trifluoromethylindoline (D10)

A mixture of 5-methoxy-6-trifluoromethylindoline (D9, 7.5 g, 34.3 mmol) and iodotrimethylsilane (12.5 ml, 89.3 mmol) in dry chloroform (70 ml) was heated under reflux for 65 h. Methanol was then added cautiously with stirring to the cooled mixture, and solvent was then removed in vacuo. The residue was treated with saturated sodium bicarbonate solution and water until basic, and then extracted with dichloromethane/methanol. The organic extract was washed with brine, dried and evaporated. The residue was extracted with ether in a Soxhlet apparatus, and concentration of the resultant solution gave the title compound in three crops (total 2.85 g, 41%), m.p.>180° (decomp.).

$^1$H NMR ($CDCl_3/CD_3OD$) δ: 3.02 (2H, d, J=8), 3.52 (2H, d, J=8), 4.00 (3H, s), 6.77 (1H, s), 6.83 (1H, s).

DESCRIPTION 11

1-Acetyl-5-hydroxy-6-trifluoromethylindoline (D11)

A mixture of indoline (D10, 2.84 g, 14 mmol) and acetic anhydride (1.32 ml, 14 mmol) in dry dichloromethane (50 ml) was stirred at room temperature for 3 h, then evaporated. The residue was treated cautiously with saturated sodium bicarbonate solution, then the solid product was filtered off, washed with water and dried to give the title compound (3.28 g, 96%), m.p. 244–7° C.

1H NMR ($d_6$-DMSO) δ: 2.10 (3H, s), 3.11 (2H, t, J=8), 4.06 (2H, t, J=8), 6.88 (1H, s), 8.18 (1H, s).

DESCRIPTION 12

1-Acetyl-6trifluoromethyl-5-trifluoromethylsulphonyloxy-indoline (D12)

To a solution of the acetylindoline (D11, 1.19 g, 4.9 mmol) in dry pyridine (10 ml) at 0° C. was added trifluoromethanesulphonic anhydride (1.52 g, 5.4 mmol). The mixture was then stirred overnight, while slowly warming to room temperature. The mixture was partially evaporated, the residual liquor was diluted well with water and the precipitate was filtered off. The crude product was dissolved in dichloromethane and the solution was washed with 1N hydrochloric acid and brine, dried and evaporated to give the title compound (1.77 g, 96%).

$^1$H NMR (CDCl$_3$) δ: 2.28 (3H, s), 3.32 (2H, t, J=8), 4.19 (2H, t, J=8), 7.29 (1H, s), 8.60 (1H, s).

MS m/z=378 (MH$^+$)

DESCRIPTION 13

5-Methyl-6-trifluoromethylindoline (D13)

To a mixture of the trifluoromethylsulphonyloxyindoline (D12, 1.77 g, 4.69 mmol), lithium chloride (0.60 g, 14.1 mmol) and bis(triphenylphosphine) palladium (II) chloride (0.10 g, 0.14 mmol) in dry dimethylformamide (15 ml) was added tetramethyltin (0.72 ml, 5.2 mmol). The mixture was heated at 110° C. for 3.5 h, then cooled and evaporated. The residue was partitioned between dichloromethane and water, and the organic phase was washed with brine, dried and evaporated. The crude product was dissolved in ethanol (30 ml), 10% aqueous sodium hydroxide solution (7.5 ml) and solid sodium hydroxide (1 g) were added and the mixture was heated under reflux overnight. Ethanol was removed in vacuo, and the residue was diluted with water and extracted with dichloromethane. The organic extract was washed with brine, dried and evaporated. The residue was chromatographed on silica gel (50 g), eluted under suction with 2:1 ether/petroleum ether to give the title compound (0.70 g, 74%), m.p. 43–4° C.

$^1$H NMR (CDCl$_3$) δ: 2.34 (3H, s), 3.02 (2H, t, J=8), 3.57 (2H, t, J=8), 3.78 (1H, broad), 6.85 (1H, s), 7.00 (1H, s).

DESCRIPTION 14

3-Methyl-5-nitro-2-(pyridin-2-ylmethyloxy)pyridine (D14)

2-Pyridylcarbinol (1.96 g, 18 mmol) in dry dimethylformamide (20 ml) was cooled to −20° C. and treated with sodium hydride (0.48 g of 80% dispersion in mineral oil, 16 mmol). The mixture was stirred under argon at −20° C. for one hour then a solution of 2-chloro-3-methyl-5-nitropyridine (2.07 g, 12 mmol) in dry dimethylformamide (10 ml) was added and the mixture was allowed to warn to room temperature over 16 hours. The solvent was removed in vacuo and the residue partitioned between dichloromethane (3×100 ml) and 10% aqueous sodium hydroxide solution(75 ml). The combined organics were dried (Na$_2$SO$_4$) and evaporated in vacuo to a residue which was subjected to flash column chromatography with 1:1 ethyl acetate/petroleum ether as eluant to afford the title compound (1.47 g, 51%) as lemon yellow crystals.

$^1$H NMR (250 MHz, CDCl$_3$) δ (ppm): 2.38 (3H, s), 5.63 (2H, s), 7.25 (1H, m), 7.43 (1H, d, J=8), 7.71 (1H, m, J=8,1), 8.22 (1H, d, J=2), 8.62 (1H, d, J=5), 8.92 (1H, d, J=2).

DESCRIPTION 15

5-Amino3-methyl-2-(pyridin-2-ylmethyloxy)pyridine (D15)

3-Methyl-5-nitro-2-(pyridin-2-ylmethyloxy)pyridine (D14, 1.42 g, 5.8 mmol) in ethanol (100 ml) was treated dropwise with a solution of tin (II) chloride (5.68 g) in conc. HCl (10 ml) at 60° C. The mixture was stirred at 60° C. for one hour, then cooled, diluted with water and basified with 40% aqueous sodium hydroxide solution. The aqueous solution was extracted with dichloromethane (3×100 ml), dried (Na$_2$SO$_4$) and evaporated in vacuo to afford the title compound (1.24 g, 100%) as a brown liquid.

$^1$H NMR (250 MHz, CDCl$_3$) δ (ppm): 2.23 (3H, s), 5.44 (2H, s), 6.90 (1H, t, J=13), 7.18 (1H, t, J=7), 7.44 (1H, d, J=8), 7.48 (1H, d, J=8), 7.68 (1H, m, J=7), 8.59 (1H, d, J=4).

EXAMPLE 1

5-Methyl-1-[2-(pyridin-2-ylmethyloxy)pyridin-5-ylcarbamoyl]-6-trifluoromethylindoline (E1)

A mixture of indoline (D13, 0.30 g, 1.49 mmol), phenylcarbamate (D3, 0.48 g, 1.5 mmol) and triethylamine (0.20 ml, 1.5 mmol) in dry acetonitrile (10 mL) was warmed briefly to ensure complete solution of reactants, then stirred overnight at room temperature. The mixture was poured into water (50 ml) and the precipitate was filtered off, washed with water and dried. The crude product was chromatographed on silica gel (25 g) eluted with 4% methanol/dichloromethane. Eluted product was recrystallised from dichloromethane/methanol to give the title compound (0.35 g, 55%), m.p. 219–20° C.

NMR ($d_6$-DMSO) δ: 2.36 (3H, s), 3.22 (2H, t, J=8), 4.15 (2H, t, J=8), 5.40 (2H, s), 6.93 (1H, d, J=8), 7.25 (1H, s), 7.32 (1H, dd, J=7,5), 7.45 (1H, d, J=7), 7.80 (1H, t, J=7), 7.90 (1H, dd, J=8,2), 8.15 (1H, s), 8.23 (1H, d, J=2), 8.57 (1H, d, J=5), 8.67 (1H,s)

EXAMPLE 2

1-[2-(Pyridin-2-ylmethyloxy)pyridin-5-ylcarbamoyl]-5trifluoromethylindoline E2)

Phenyl N-[2-(pyridin-2-ylmethyloxy)pyridin-5-yl] carbamate (D3, 0.20 g, 0.62 mmol) in dry dimethylformamide (10 ml) was treated with 5-trifluoromethylindoline (D6, 0.12 g, 0.62 mmol) and heated at 100° C. for 1 hour. After cooling to ambient temperature, the solvent was removed in vacuo. The residue was dissolved in dichloromethane, washed with 10% aqueous sodium hydroxide solution, dried (Na$_2$SO$_4$) and evaporated in vacuo. The resulting oil was chromatographed on silica gel eluting with 2% methanol/dichloromethane and triturated with diethyl ether to afford the title compound (0.08 g, 31%) as an off-white solid.

$^1$H NMR (250 MHz; $d_6$DMSO) δ (ppm): 3.28 (2H, t, J=10), 4.19 (2H, t, J=10), 5.40 (2H, s), 6.94 (1H, d, J=10), 7.28–7.37 (1H, m), 7.40–7.58 (3H, m), 7.82 (1H, dt, J=2,7), 7.90 (1H, dd, 3=2,7), 8.00 (1H, d, J=10), 8.26 (1H, d, J=3), 8.56 (1H, d, J=7), 8.75 (1H, s).

EXAMPLE 3

5-Methyl-1-[2-(pyridin-2-ylmethyloxy)3-methylpyridin-5-ylcarbamoyl]-6-trifluoromethylindoline (E3)

5-Amino-3-methyl-2(pyridin-2-ylmethyloxy)pyridine (D15, 0.5 g, 2.3 mmol) in dichloromethane (30 ml) was cooled to −20° C. under argon. Triethylamine (0.32 ml, 2.3 mmol) was added, followed dropwise by phenyl chloroformate (0.35 ml, 2.8 mmol). The mixture was warmed to room temperature and diluted with dichloromethane (100 ml) then washed with aqueous sodium bicarbonate (50 ml), dried ($Na_2SO_4$) and evaporated in vacuo to give phenyl N-2-[3-methyl-(pyridin-2-ylmethyloxypyridin-5-yl]carbamate. The crude carbamate was treated with 5-methyl-6-trifluoromethylindoline (D7, 0.47 g, 0.0023 mol, 1 eq) and triethylamine (1 ml) in DMF (30 ml) at 100° C. under argon for 2 hours then allowed to cool. Solvent was removed in vacuo and the residue was partitioned between dichloromethane (3×100 ml) and 10% aqueous sodium hydroxide (50 ml). The combined organics were dried ($Na_2SO_4$) and evaporated in vacuo to give the crude product which was subjected to flash chromatography using 5% methanol/dichloromethane as eluant and recrystallised from dichloromethane/60–80° C. petroleum ether to afford the title compound (0.27 g, 28%) as white crystals. m.p. 188–189° C.

$^1$H NMR (250 MHz, $CDCl_3$) δ (ppm): 2.29 (3H, s), 2.40 (3H, s), 3.25 (2H, t, J=9), 4.09 (2H, t, J=9), 5.51 (2H, s), 6.36 (1H, br s), 7.07 (1H, s), 7.20 (1H, t, J=7), 7.43 (1H, d, J=8), 7.68 (1H, m, J=7,1), 7.77 (1H, d, J=1), 7.82 (1H, d, J=1), 8.23 (1H, s), 8.59 (1H, d, J=4).

MS m/z=443 ($MH^+$)

EXAMPLE 4

5-Bromo-1-[2-(pyridin-2-ylmethyloxy)pyridin-5-ylcarbamoyl]-indoline (E4)

Phenyl N-[2-(pyridin-2-ylmethyloxy)pyridin-5-yl] carbamate (D3) and 5-bromoindoline were converted into the title compound using a method similar to that of Example 1, m.p. 138–139° C.

EXAMPLE 5

1-[2-(pyridin-2-ylmethyloxy)pyridin-5ylcarbamoyl]-6-trifluoromethyl-indoline (E5)

Phenyl N-[2-(pyridin-2-ylmethyloxy)pyridin-5-yl] carbamate (D3) and 6-trifluoromethylindoline (WO 96/23783) were converted into the title compound using a method similar to that of Example 1, m.p. 178–179° C.
Pharmacological data
[$^3$H]-mesulergine binding to rat or human 5-$HT_{2C}$ clones expressed in 293 cells in vitro Compounds can be tested following the procedure outlined in WO 94/04533. The compounds of the Examples had pKi of about 8.6 to 9.5 in human cells.
Reversal of MCPP-induced Hypolocomotion Compounds can be tested following the procedure outlined in WO 94/04533. The compounds of the Examples showed good activity after dosing at 1–5 mg/kg p.o. in the rat with an extended duration of action.

What is claimed is:

1. A compound of formula (I) or a salt thereof:

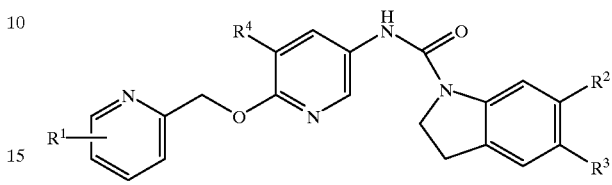

wherein:
$R^1$ is hydrogen or $C_{1-6}$ alkyl;
$R^2$, $R^3$ and $R^4$ groups are independently hydrogen, halogen or $C_{1-6}$ alkyl optionally substituted by one or more fluorine atoms.

2. A compound according to claim 1 in which $R^1$ is hydrogen.

3. A compound according to claim 2 in which $R^2$ is hydrogen or $CF_3$.

4. A compound according to claim 3 in which $R^3$ is hydrogen, bromine, $CF_3$ or methyl.

5. A compound according to claim 4 in which $R^4$ is hydrogen or $C_{1-6}$ alkyl.

6. A compound according to claim 1 which is:
5-Methyl-1-[2-pyridin-2-ylmethyloxy)pyridin-5-ylcarbamoyl]-6-trifluoromethylindoline, 1-[2-(pyridin-2-ylmethyloxy)pyridin-5-ylcarbamoyl]-5-trifluoromethylindoline, 5-Methyl-1-[2-(pyridin-2-ylmethyloxy)-3-methylpyridin-5-ylcarbamoyl]-6-trifluoromethylindoline, 5-Bromo-1-[2-(pyridin-2-ylmethyloxy)pyridin-5ylcarbamoyl]-indoline, 1-[2-(pyridin-2-ylmethyloxy)pyridin-5-ylcarbamoyl]-6-trifluoromethyl-indoline, or a pharmaceutically acceptable salt thereof.

7. A pharmaceutical composition which comprises a safe and pharmaceutically effective amount of a compound according to claim 1 and a pharmaceutically acceptable carrier or excipient.

8. A method of treating anxiety and/or depression comprising administering to a subject in need of treatment a safe and effective amount of a compound according to claim 1.

9. A compound according to claim 6 which is:
5-Methyl-1-[2-(pyridin-2-ylmethyloxy)pyridin-5-ylcarbamoyl]-6- trifluoromethylindoline.

10. A pharmaceutical composition which comprises a safe and pharmaceutically effective amount of 5-Methyl-1-[2 (pyridin-2-ylmethyloxy)pyridin-5-ylcarbamoyl]-6-trifluoromethylindoline or a pharmaceutically acceptable salt thereof and a pharmaceutically acceptable carrier or excipient.

* * * * *